(12) United States Patent
Xu

(10) Patent No.: US 12,251,408 B2
(45) Date of Patent: Mar. 18, 2025

(54) POSTBIOTIC PREPARATION FOR PELVIC FLOOR MUSCLE REHABILITATION AND PREPARATION METHOD AND APPLICATION THEREOF

(71) Applicant: SHANDONG NICE HEALTH TECHNOLOGY CO., LTD., Shandong (CN)

(72) Inventor: Yuan Xu, Jinan (CN)

(73) Assignee: SHANDONG NICE HEALTH TECHNOLOGY CO., LTD., Jinan (CN)

( * ) Notice: Subject to any disclaimer, the term of this patent is extended or adjusted under 35 U.S.C. 154(b) by 0 days.

(21) Appl. No.: 18/408,667

(22) Filed: Jan. 10, 2024

(65) Prior Publication Data

US 2024/0366692 A1    Nov. 7, 2024

(30) Foreign Application Priority Data

May 6, 2023  (CN) .......................... 202310502907.7

(51) Int. Cl.
| | |
|---|---|
| *A61K 35/747* | (2015.01) |
| *A61K 9/00* | (2006.01) |
| *A61P 21/00* | (2006.01) |
| *C12N 1/20* | (2006.01) |
| *C12R 1/25* | (2006.01) |

(52) U.S. Cl.
CPC .......... *A61K 35/747* (2013.01); *A61K 9/0053* (2013.01); *A61P 21/00* (2018.01); *C12N 1/205* (2021.05); *C12R 2001/25* (2021.05)

(58) Field of Classification Search
None
See application file for complete search history.

(56) References Cited

U.S. PATENT DOCUMENTS

2014/0322273 A1   10/2014   Ai et al.

FOREIGN PATENT DOCUMENTS

| CN | 106520633 A | 3/2017 |
| JP | 2020-176094 A | 10/2020 |
| WO | 2023/071194 A1 | 5/2023 |

OTHER PUBLICATIONS

Milandri et al., "Effectiveness of D-mannose, Hibiscus sabdariffa and Lactobacillus plantarum Therapy in Prevention of Infectious Events Following Urodynamic Study", Urologia Journal, 2018.

*Primary Examiner* — Vera Afremova
(74) *Attorney, Agent, or Firm* — Oliff PLC

(57) ABSTRACT

A postbiotic preparation for pelvic floor muscle rehabilitation and a preparation method and application thereof. A strain of *Lactobacillus plantarum* Nice-02 is successfully obtained, and a postbiotic preparation product is successfully developed based on the strain.

11 Claims, No Drawings

POSTBIOTIC PREPARATION FOR PELVIC FLOOR MUSCLE REHABILITATION AND PREPARATION METHOD AND APPLICATION THEREOF

TECHNICAL FIELD

The present disclosure belongs to the technical field of microorganism and biological medicine, and particularly relates to a postbiotic preparation for pelvic floor muscle rehabilitation and a preparation method and application thereof.

BACKGROUND

Information of the Related Art part merely disclosed is only to enhance the understanding of the overall background of the present disclosure, but is not necessarily regarded as acknowledging or suggesting, in any form, that the information constitutes the prior art known to a person of ordinary skill in the art.

Female pelvic floor muscles (PFMs) spread across the pelvic outlet, support the pelvis and abdominal internal organs, help control urination and defecation, and achieve sexual functions. In human bodies, the PFMs include the levator ani muscle complexus, which consists of portions at the inner sides (puborectalis) and outer sides (Musculi pubococcygeus) of the pectineal muscles and the Musculus iliococcygeus and posterior caudal muscles. The PFM dysfunction is one of main reasons for pelvic floor disease development, including pelvic organ prolapse, uroclepsia and fecal incontinence. Factors such as senility, fetation and vaginal delivery may cause pelvic floor muscle contractility reduction or structural injury, the pelvic floor support structure cannot resist the abdominal pressure, and stress urinary incontinence and pelvic floor organ prolapse are finally caused. The SUI (stress urinary incontinence) is called as invisible "social cancer", belongs to a common frequently-occurring disease in middle-aged and old women, and is defined as a symptom of uncontrollable urine leakage under abdominal pressure increase conditions such as cough and laugh. When the symptom occurs, it has high privacy, patients are often too shy to speak out or cannot get help, and great negative influence is caused on the life, interpersonal relationship and mental health of the patients.

The therapy methods of the pelvic floor dysfunction diseases include conservative treatment, medicine treatment and surgical treatment at present. The conservative treatment includes pad, catheter or urinal, weight loss, smoking cessation, behavior treatment (bladder training, liquid/diet change and caffeine intake reduction), physical therapy, pelvic floor electrophysiological stimulation, etc. However, effects of the conservative treatment are not ideal due to lack of motivation, lack of continuity and execution inconsistency. Anticholinergic drug and/or β-3 receptor stimulants are most common medicine for mixed urinary incontinence, but the side effects are great after long-period medicine taking. There are many options for surgery, such as paraurethral injection therapy, tension-free vaginal tape therapy, pubis vaginal or middle urethra tape therapy, Burch colposuspension, etc. However, these options may only offer short-term relief. In the long term, they may generally cause complications, such as bladder or vaginal perforation, urination or urine storage dysfunction, chronic pelvic pain, urethra and vaginal erosion or infection, etc.

At present, besides the three above methods in medicine, there is no method capable of fast and effectively solving the female pelvic floor muscle problem. However, the above treatment methods have the defects that the cost is high, and secret problems such as postoperation pain, infection and inflammation may easily occur. Most women are often too shy to speak out the pelvic floor muscle problems, and are afraid of visiting a doctor by themselves. Therefore, gradually solving the pelvic floor muscle problems by orally taking a conditioning agent is a better solution. Based on the above analysis, the advantages of pelvic floor muscle rehabilitation through orally taking postbiotic are obviously superior to medical treatment.

SUMMARY

Based on the defects in the prior art, the present disclosure provides a postbiotic preparation for pelvic floor muscle rehabilitation and a preparation method and application thereof. Through verification by experiments on animals and humans, the postbiotic preparation prepared by the present disclosure has the effects of promoting smooth muscle contraction and repairing injured pelvic floor muscles and thus effectively solves the problems of an existing therapeutic method of great side effects, poor treatment effect, poor patient compliance, etc. Based on the above study results, the present disclosure is completed.

To achieve the foregoing technical objectives, the present disclosure adopts the following technical solutions:

In a first aspect of the present disclosure, the present disclosure provides a strain of *Lactobacillus plantarum* Nice-02 preserved in CCTCC (China Center for Type Culture Collection) (address: Wuhan University, Luojiashan, Wuchang, Wuhan, Hubei Province) on Apr. 21, 2023 with a biological preservation number of CCTCC NO: M 2023571.

In a second aspect of the present disclosure, the present disclosure provides a microbial agent, at least including the *L. plantarum* and/or a fermentation metabolite of the *L. plantarum*.

Further, the microbial agent includes an inactivated *L. plantarum* and/or a fermentation metabolite of the inactivated *L. plantarum*. The fermentation metabolite includes but is not limited to exopolysaccharides, polypeptide and amino acid. In this case, the microbial agent is a postbiotic preparation.

Therefore, in a third aspect, the present disclosure provides a preparation method of the microbial agent. The preparation method includes:

S1: activation culture: performing plate streaking on the *Lactobacillus plantarum* Nice-02 into an activation culture medium to obtain a pure strain;

S2: primary seed solution preparation: picking and placing a single colony of the *L. plantarum* Nice-02 prepared in S1 into a first culture solution at 28 to 30° C. for stationary culture for 12 to 14 h to obtain a primary seed solution;

S3: secondary seed solution preparation: inoculating the primary seed solution into a second culture solution according to an inoculation amount of 0.1 to 5% (preferably 0.5%, v/v) for stationary culture at 30° C. to 40° C. (preferably 37° C.) for 10 to 12 h to obtain a secondary seed solution;

S4: tertiary seed solution preparation: inoculating the cultured secondary seed solution into a seeding tank containing a third culture solution under an aseptic condition at an inoculation amount of 0.5 to 5% (preferably 2%), and performing stir culture at a stirring speed of 20 to 50 r/min (preferably 30 r/min), a temperature of 30° C. to 40° C. (preferably 37° C.), a pH value of 7.0 and a tank pressure of 0.03 to 0.06 MPa (preferably 0.05 Mpa) to obtain a tertiary seed solution after the culture for 10 to 12 h;

S5: *L. plantarum* primary fermentation: inoculating the tertiary seed solution into a fermentation tank containing a sterilized culture solution at an inoculation amount of 0.5 to 5% (preferably 2%), a temperature of 32° C., a stirring speed of 40 to 50 r/min (preferably 45 r/min) to be cultured for 5 to 6 h;

S6: *L. plantarum* secondary fermentation: after 5 to 6 h, lowering the fermentation temperature to 30° C., accelerating the stirring speed to 50 to 70 r/min (preferably 60 r/min), keeping the tank pressure at 0.05 MPa and the natural pH, and performing fermentation for 3 to 4 h;

S7: *L. plantarum* tertiary fermentation: after 8 to 10 h, keeping the stirring speed unchanged, raising the fermentation temperature to 35° C., keeping the tank pressure at 0.05 MPa, keeping the pH value at 6.5, and performing fermentation for 2 h;

S8: *L. plantarum* quaternary fermentation: after 10 to 12 h, decelerating the stirring speed to 30 to 40 r/min (preferably 40 r/min), raising the fermentation temperature to 40° C., keeping the tank pressure at 0.05 MPa and the pH value at 6.5, and performing fermentation for 1 to 2 h; and S9: *L. plantarum* quinary fermentation: after 11 to 14 h, keeping the stirring speed unchanged, raising the temperature to 45° C., adding sterile lipoteichoic acid accounting for 0.05 to 0.2% (preferably 0.1%) of the volume of the fermentation solution into the fermentation tank, lowering the temperature to 20° C., and keeping the state for 30 min.

According to the fourth aspect of the present disclosure, the present disclosure provides application of the postbiotic preparation to preparation of a pelvic floor muscle rehabilitation product.

The pelvic floor muscle rehabilitation product may be food or medicine.

The one or a plurality of technical solutions have the following beneficial technical effects:

According to the technical solution, a strain of *L. plantarum* is screened and obtained, and a postbiotic preparation product is successfully developed based on the strain. Through being proved by experiments, the product has the effects of promoting smooth muscle contraction, repairing injured pelvic floor muscles and fast relieving stress urinary incontinence. At the same time, by optimizing the condition parameters of a preparation process of the postbiotic preparation and performing layered fermentation on the *L. plantarum*, the advantages of fermentation period reduction and comprehensive and rich metabolites are realized, so that the postbiotic preparation is more suitable for industrialized production and thus has good practical application values.

DETAILED DESCRIPTION

It should be noted that, the following detailed descriptions are all exemplary, and are intended to provide further descriptions of the present disclosure. Unless otherwise specified, all technical and scientific terms used herein have the same meanings as those usually understood by a person of ordinary skill in the art to which the present disclosure belongs.

It should be noted that the terms used herein are merely used for describing specific implementations, and are not intended to limit exemplary implementations of the present disclosure. As used herein, the singular form is intended to include the plural form, unless the context clearly indicates otherwise. In addition, it should further be understood that terms "comprise" and/or "include" used in this specification indicate that there are features, steps, operations, devices, components, and/or combinations thereof.

In a specific implementation of the present disclosure, the present disclosure provides a strain of *Lactobacillus plantarum* Nice-02 preserved in CCTCC (China Center for Type Culture Collection) (address: Wuhan University, Luojiashan, Wuchang, Wuhan, Hubei Province) on Apr. 21, 2023 with a biological preservation number of CCTCC NO: M 2023571.

In a second aspect of the present disclosure, the present disclosure provides a microbial agent, at least including the *L. plantarum* and/or a fermentation metabolite of the *L. plantarum*.

Further, the microbial agent includes an inactivated *L. plantarum* and/or a fermentation metabolite of the inactivated *L. plantarum*. The fermentation metabolite includes but is not limited to exopolysaccharides, polypeptide and amino acid. In this case, the microbial agent is a postbiotic preparation.

Therefore, in a third aspect, the present disclosure provides a preparation method of the microbial agent. The preparation method includes:

S1: activation culture: the *Lactobacillus plantarum* Nice-02 is subjected to plate streaking into an activation culture medium to obtain a pure strain.

The activation culture medium is prepared from 0.05 to 0.2% of casein, 0.05 to 0.2% of sialic acid, 0.3 to 1.0% of beef extracts, 0.5 to 2% of peptone, 0.05 to 0.2% of sodium acetate, 0.05 to 0.2% of potassium dihydrogen phosphate and 1.5 to 2.0% of agar powder, and a pH value is adjusted to 7.0.

More specifically, the activation culture medium is prepared from 0.1% of casein, 0.1% of sialic acid, 0.7% of beef extracts, 1% of peptone, 0.1% of sodium acetate, 0.1% of potassium dihydrogen phosphate and 2.0% of agar powder, and the pH value is adjusted to 7.0.

S2: primary seed solution preparation: a single colony of the *L. plantarum* Nice-02 prepared in S1 is picked and placed into a first culture solution at 28 to 30° C. for stationary culture for 12 to 14 h to obtain a primary seed solution.

the first culture solution is prepared from 0.05 to 0.2% of casein, 0.05 to 0.2% of sialic acid, 1 to 5% of fructooligosaccharide, 0.1 to 1% of yeast powder, 0.05 to 0.2% of sodium acetate and 0.05 to 0.2% of potassium dihydrogen phosphate, and a pH value is adjusted to 7.0.

More specifically, the first culture solution is prepared from 0.1% of casein, 0.1% of sialic acid, 3% of fructooligosaccharide, 0.5% of yeast powder, 0.1% of sodium acetate and 0.1% of potassium dihydrogen phosphate, and the pH value is adjusted to 7.0.

S3: secondary seed solution preparation: the primary seed solution is inoculated into a second culture solution according to an inoculation amount of 0.1 to 5% (preferably 0.5%, v/v) for stationary culture at 30° C. to 40° C. (preferably 37° C.) for 10 to 12 h to obtain a secondary seed solution.

The second culture solution is prepared from 0.1 to 1% of casein, 0.05 to 0.2% of sialic acid, 1 to 3% of fructooligosaccharide, 0.1 to 1% of yeast powder and 0.05 to 0.2% of Tween-80, and a pH value is natural.

More specifically, the second culture solution is prepared from 0.5% of casein, 0.1% of sialic acid, 1.5% of fructooligosaccharide, 0.5% of yeast powder and 0.1% of Tween-80, and the pH value is natural.

S4: tertiary seed solution preparation: the cultured secondary seed solution is inoculated into a seeding tank containing a third culture solution under an aseptic condition at an inoculation amount of 0.5 to 5% (preferably 2%), and stir culture is performed at a stirring speed of 20 to 50 r/min (preferably 30 r/min), a temperature of 30° C. to 40° C. (preferably 37° C.), a pH value of 7.0 and a tank pressure of 0.03 to 0.06 MPa (preferably 0.05 Mpa) to obtain a tertiary seed solution after the culture for 10 to 12 h.

The third culture solution is prepared from 0.5 to 5% of peptone, 1 to 5% of isomaltooligosaccharide, 0.1 to 0.5% of dipotassium phosphate, 0.5 to 5% of glycine, 0.1 to 1% of tyrosine, 0.05 to 0.2% of Tween-80 and 0.05 to 0.2% of a polyether defoamer, and a pH value is natural.

More specifically, the third culture solution is prepared from 1% of peptone, 4% of isomaltooligosaccharide, 0.2% of dipotassium phosphate, 1% of glycine, 0.5% of tyrosine, 0.1% of Tween-80 and 0.1% of a polyether defoamer, and the pH value is natural.

S5: *L. plantarum* primary fermentation: the tertiary seed solution is inoculated into a fermentation tank containing a sterilized culture solution at an inoculation amount of 0.5 to 5% (preferably 2%), a temperature of 32° C., a stirring speed of 40 to 50 r/min (preferably 45 r/min) to be cultured for 5 to 6 h.

The culture solution is prepared from 3% of isomaltooligosaccharide, 0.2% of casein, 2% of peptone, 5% of fructooligosaccharide, 3% of water-soluble starch, 0.1% of Tween-80, 0.5% of glycine, 0.5% of tyrosine and 0.2% of a polyether defoamer, and a pH value is natural.

S6: *L. plantarum* secondary fermentation: after 5 to 6 h, the fermentation temperature is lowered to 30° C., the stirring speed is accelerated to 50 to 70 r/min (preferably 60 r/min), the tank pressure is kept at 0.05 MPa, the pH value is kept natural, and fermentation is performed for 3 to 4 h.

S7: *L. plantarum* tertiary fermentation: after 8 to 10 h, the stirring speed is kept unchanged, the fermentation temperature is raised to 35° C., the tank pressure is kept at 0.05 MPa, the pH value is kept at 6.5, and fermentation is performed for 2 h.

S8: *L. plantarum* quaternary fermentation: after 10 to 12 h, the stirring speed is decelerated to 30 to 40 r/min (preferably 40 r/min), the fermentation temperature is raised to 40° C., the tank pressure is kept at 0.05 MPa, the pH value is kept at 6.5, and fermentation is performed for 1 to 2 h.

S9: *L. plantarum* quinary fermentation: after 11 to 14 h, the stirring speed is kept unchanged, the temperature is raised to 45° C., sterile lipoteichoic acid accounting for 0.05 to 0.2% (preferably 0.1%) of the volume of the fermentation solution is added into the fermentation tank, and the temperature is lowered to 20° C. for 30 min.

The preparation method further includes performing high-temperature inactivation and spray drying on the fermentation solution prepared in S9. The high-temperature inactivation specifically includes: inactivation treatment is performed after the state maintenance for 40 min at 75° C., and spray drying may be performed after temperature lowering. For the spray drying, an air inlet temperature is set to be 150° C. to 180° C., an air outlet temperature is set to be 90° C. to 100° C., and postbiotic preparation powder is prepared after the spray drying.

In another implementation of the present disclosure, the present disclosure provides application of the postbiotic preparation to preparation of a pelvic floor muscle rehabilitation product.

The pelvic floor muscle rehabilitation product may be food or medicine.

More specifically, the medicine may include at least one of other medicine inactive ingredients.

The medicine inactive ingredients may be carriers, excipients, diluents, etc. commonly used in medicine. Additionally, according to a general method, they may be made into an oral preparation of powder, granules, suspensions, emulsion, syrup, spray, etc.

The non-medical active ingredients such as the carriers, the excipients and the diluents capable of being included are well known in the field, and may be determined to conform to the clinical standard by those of ordinary skill in the art.

In another specific implementation of the present disclosure, the carriers, the excipients and the diluents include but are not limited to lactose, glucose, saccharose, sorbitol, mannitol, xylitol, erythritol, maltitol, starch, arabic gum, alginate, gelatin, calcium phosphate, calcium silicate, cellulose, methylcellulose, microcrystalline cellulose, polyvinylpyrrolidone, water, methyl hydroxybenzoate, nipasol, talcum powder, magnesium stearate, mineral oil, etc.

The following embodiments are used to further explain the present disclosure, but are not intended to limit the present disclosure. It should be understood that the embodiments herein are provided for describing the present disclosure and not intended to limit the scope of the present disclosure. In the embodiments, "%" of ingredients in each culture medium (solution) represents mass percentage in volume, and the unit is g/mL.

Embodiment 1

A preparation method of postbiotic for pelvic floor muscle rehabilitation included:

On a clean bench, *Lactobacillus plantarum* Nice-02 preserved in a −80° C. low-temperature refrigerator was subjected to plate streaking to a culture medium plate, a single colony was screened, and the single colony was repeatedly activated for 3 times to obtain a pure strain.

The composition of the culture medium was as follows: 0.1% of casein, 0.1% of sialic acid, 0.7% of beef extracts, 1% of peptone, 0.1% of sodium acetate, 0.1% of potassium dihydrogen phosphate and 2.0% of agar powder were contained in per 100 mL of the culture medium, and a pH value was adjusted to 7.0 with potassium hydroxide.

The single colony was picked and placed into a 100 mL of a liquid culture medium (the culture medium was placed into a 15*200 test tube. The composition of the liquid culture medium was as follows: 0.1% of casein, 0.1% of sialic acid, 3% of fructooligosaccharide, 0.5% of yeast powder, 0.1% of sodium acetate and 0.1% of potassium dihydrogen phosphate were contained in per 100 mL of the culture medium, and a pH value was adjusted to 7.0 with potassium hydroxide), and stationary culture was performed at 30° C. for 12 h.

The above cultured seed solution was inoculated into a triangular flask culture medium at an inoculation amount of 0.5%. That was, 0.5 mL of the primary seed solution was inoculated into per 100 mL of the secondary seed culture solution (0.5% of casein, 0.1% of sialic acid, 1.5% of fructooligosaccharide, 0.5% of yeast powder and 0.1% of Tween-80 were contained in per 100 mL of the culture solution). After the inoculation, a bottle opening was sealed by sterile gauze and kraft paper, the inoculated strain was uniformly mixed with the culture solution through slight shaking by hand. Then, the mixture was placed into a thermostat for stationary culture under the condition of 37° C. for 12 h. The obtained solution was called as the secondary seed solution.

The cultured secondary seed solution was inoculated into a seeding tank of a tertiary seed culture solution (1% of peptone, 4% of isomaltooligosaccharide, 0.2% of dipotassium phosphate, 1% of glycine, 0.5% of tyrosine, 0.1% of Tween-80 and 0.1% of a polyether defoamer were contained in per 100 mL of the culture medium, and a pH value was natural) under the aseptic condition at an inoculation amount of 2% (v/v), and stir culture was performed at a stirring speed of 30 r/min, a temperature of 37° C., a pH value of 7.0 and a tank pressure of 0.05 MPa for 12 h.

The tertiary seed solution was inoculated into a fermentation tank containing a sterilized fermentation solution (3% of isomaltooligosaccharide, 0.2% of casein, 2% of peptone, 5% of fructooligosaccharide, 3% of water-soluble starch, 0.1% of Tween-80, 0.5% of glycine, 0.5% of tyrosine and 0.2% of a polyether defoamer were contained in per 100 mL of the culture medium, and a pH value was natural) at an inoculation amount of 2% (v/v), a temperature of 32° C. and a stirring speed of 45 r/min to be cultured for 5 h. After 5 h, the fermentation temperature was lowered to 30° C., the stirring speed was raised to 60 r/min, the tank pressure was kept at 0.05 MPa, the pH value was natural, and the fermentation was performed for 3 h. After 8 h, the stirring speed was unchanged, the fermentation temperature was raised to 35° C., the tank pressure was kept at 0.05 MPa, the pH value was kept at 6.5 through an automatic pH regulation and control system, and the fermentation was performed for 2 h. After 10 h, the stirring speed was lowered to 40 r/min, the fermentation temperature was raised to 40° C., the tank pressure was kept at 0.05 MPa, the pH value was kept at 6.5 through an automatic pH regulation and control system, and the fermentation was performed for 1h. After 11 h, the stirring speed was unchanged, the temperature was raised to 45° C., sterile lipoteichoic acid accounting for 0.1% of the fermentation tank was added into the fermentation tank, the temperature was lowered to 20° C. for 30 min, then, the temperature was raised to 75° C. for 40 min for inactivation, and next, the temperature was lowered to 30° C.

An air inlet temperature was set to be 150° C. to 180° C., an air outlet temperature was set to be 90° C. to 100° C., and postbiotic powder was obtained after spray drying.

The postbiotic obtained according to Embodiment 1 contained 24% of exopolysaccharides, 20.8% of polypeptide and 38.5% of amino acid.

Embodiment 2

A preparation method of postbiotic for pelvic floor muscle rehabilitation included:

On a clean bench, *Lactobacillus plantarum* Nice-02 preserved in a −80° C. low-temperature refrigerator was subjected to plate streaking to a culture medium plate, a single colony was screened, and the single colony was repeatedly activated for 3 times to obtain a pure strain.

The composition of the culture medium was as follows: 0.1% of casein, 0.1% of sialic acid, 0.7% of beef extracts, 1% of peptone, 0.1% of sodium acetate, 0.1% of potassium dihydrogen phosphate and 2.0% of agar powder were contained in per 100 mL of the culture medium, and a pH value was adjusted to 7.0 with potassium hydroxide.

The single colony was picked and placed into a 100 mL of a liquid culture medium (the culture medium was placed into a 15*200 test tube. The composition of the liquid culture medium was as follows: 0.1% of casein, 0.1% of sialic acid, 3% of fructooligosaccharide, 0.5% of yeast powder, 0.1% of sodium acetate and 0.1% of potassium dihydrogen phosphate were contained in per 100 mL of the culture medium, and a pH value was adjusted to 7.0 with potassium hydroxide), and stationary culture was performed at 30° C. for 12 h.

The above cultured seed solution was inoculated into a triangular flask culture medium at an inoculation amount of 0.5%. That was, 0.5 mL of the primary seed solution was inoculated into per 100 mL of the secondary seed culture solution (0.5% of casein, 0.1% of sialic acid, 1.5% of fructooligosaccharide, 0.5% of yeast powder and 0.1% of Tween-80 were contained in per 100 mL of the culture solution). After the inoculation, a bottle opening was sealed by sterile gauze and kraft paper, the inoculated strain was uniformly mixed with the culture solution through slight shaking by hand. Then, the mixture was placed into a thermostat for stationary culture under the condition of 37° C. for 12 h. The obtained solution was called as the secondary seed solution.

The cultured secondary seed solution was inoculated into a seeding tank of a tertiary seed culture solution (1% of peptone, 4% of isomaltooligosaccharide, 0.2% of dipotassium phosphate, 1% of glycine, 0.5% of tyrosine, 0.1% of Tween-80 and 0.1% of a polyether defoamer were contained in per 100 mL of the culture medium, and a pH value was natural) under the aseptic condition at an inoculation amount of 2%, and stir culture was performed at a stirring speed of 30 r/min, a temperature of 37° C., a pH value of 7.0 and a tank pressure of 0.05 MPa for 12 h.

The tertiary seed solution was inoculated into a fermentation tank containing a sterilized fermentation solution (3% of isomaltooligosaccharide, 0.2% of casein, 2% of peptone, 5% of fructooligosaccharide, 3% of water-soluble starch, 0.1% of Tween-80, 0.5% of glycine, 0.5% of tyrosine and 0.2% of a polyether defoamer were contained in per 100 mL of the culture medium, and a pH value was natural) at an inoculation amount of 2%, a temperature of 32° C. and a stirring speed of 45 r/min to be cultured for 46 h. After 46 h, the stirring speed was unchanged, the temperature was raised to 45° C., sterile lipoteichoic acid accounting for 0.1% of the fermentation tank was added into the fermentation tank, the temperature was lowered to 20° C. for 30 min, then, the temperature was raised to 75° C. for 40 min for inactivation, and next, the temperature was lowered to 30° C.

An air inlet temperature was set to be 150° C. to 180° C., an air outlet temperature was set to be 90° C. to 100° C., and postbiotic powder was obtained after spray drying.

The postbiotic obtained according to Embodiment 2 contained 19% of exopolysaccharides, 17.8% of polypeptide and 34% of amino acid.

Effect Verification

1. In Vitro Muscle Contraction Evaluation

Duodenum smooth muscles were used as experiment objects, and the influence of the postbiotic products on the duodenum smooth muscle contraction performance was observed and determined. Experiment scheme: rats were divided into a control group and experiment groups. The rats in the control group were normally fed, the rats in experiment groups were additionally fed with 0.5% (w w), 1.0% and 1.5% postbiotic (all products prepared according to Embodiment 1, and the three experiment groups were sequentially named as Experiment groups 1 to 3) in food.

After the feeding for about 2 weeks, the rats were narcotized and killed through neck dislocation. The rat's abdomens were cut open to take intestinal canals by using stomachus pyloricus and duodenum junctions as starting points, the intestinal canals were cut into intestinal segments about 1 cm, were cleanly washed by a Krebs solution, and were placed into a Krebs solution, the moisture was preserved at a constant temperature of 37° C., the basic tension was adjusted to 1 g, and mixed gas (950 mL L$^{-1}$ oxygen and 50 mL·L$^{-1}$ carbon dioxide) was continuously introduced by using an air needle at a speed of 1 to 2 air bubbles per second. Duodenum smooth muscle contraction motion and change signals were introduced to a BL-420 Biological function test multi-channel physiological signal collection and processing system through a tonotransducer, and contraction curves were observed. The results were as shown in Table 1 below. The results in Table 1 show that the postbiotic has the function of promoting smooth muscle contraction, and shows certain dose dependency.

TABLE 1

Influence of postbiotic on rat isolated intestinal smooth muscle contraction ($\bar{x} \pm s$, n = 8)

| Group | Amplitude (g) | Frequency (hz) |
|---|---|---|
| Control group | 0.81 ± 0.14 | 0.57 ± 0.11 |
| Experimental group 1 | 1.61 ± 0.26 | 1.04 ± 0.23 |
| Experimental group 2 | 1.95 ± 0.32 | 1.412 ± 0.29 |
| Experimental group 3 | 1.72 ± 0.31 | 1.24 ± 0.41 |

2. Small-Scale Clinical Experiments on Pelvic Floor Muscle Injury Therapy 20 females with the ages between 40 to 60 participated in experiments on their own will, and completed questionnaire forms and records. People seriously troubled by stress urinary incontinence caused by pelvic floor muscle problems were in a test group. They orally took 600 mg of postbiotic (the product prepared according to Embodiment 1) on an empty stomach every day in the morning for 3 weeks. In the period, they did rope skipping to test the urine leakage condition. The original dietary habits were not changed in the test period, and the diet was normal.

After the use cycle was completed, 100% of postbiotic users expressed that they hardly adopted the jumping exercise mode before postbiotic use because urine leakage might occur after a few times of jumping, but after the postbiotic use, no urine leakage occurred in the whole rope skipping process, and they even had no urine leakage feeling.

TABLE 2

Experiment statistical table of pelvic floor muscle rehabilitation people by postbiotic

| Serial number | Condition before taking | Dosage and use cycle | Condition after taking |
|---|---|---|---|
| 1 | Urine leakage during jumping | 600 mg/day for 2 weeks | No urine leakage after 1500 times of rope skipping |
| 2 | Urine leakage during jumping | 600 mg/day for 2 weeks | No urine leakage after 1500 times of rope skipping |
| 3 | Urine leakage during jumping | 600 mg/day for 2 weeks | No urine leakage after 1500 times of rope skipping |
| 4 | Urine leakage during jumping | 600 mg/day for 2 weeks | No urine leakage after 1500 times of rope skipping |
| 5 | Urine leakage during jogging | 600 mg/day for 2 weeks | Slight urine leakage after 3 km of jogging |
| 6 | Urine leakage during cough | 600 mg/day for 2 weeks | No urine leakage during severe cough |
| 7 | Urine leakage during jogging | 600 mg/day for 2 weeks | Slight urine leakage after 3 km of jogging |
| 8 | Urine leakage during jumping | 600 mg/day for 2 weeks | Slight urine leakage after 1500 times of rope skipping |
| 9 | Urine leakage during cough | 600 mg/day for 2 weeks | No urine leakage during severe cough |
| 10 | Urine leakage during cough | 600 mg/day for 2 weeks | No urine leakage during severe cough |
| 11 | Urine leakage during jogging | 600 mg/day for 2 weeks | No urine leakage after 3 km of jogging |
| 12 | Urine leakage during jogging | 600 mg/day for 2 weeks | No urine leakage after 3 km of jogging |
| 13 | Urine leakage during jumping | 600 mg/day for 2 weeks | No urine leakage after 1500 times of rope skipping |
| 14 | Urine leakage during jumping | 600 mg/day for 2 weeks | No urine leakage after 1500 times of rope skipping |
| 15 | Urine leakage during cough | 600 mg/day for 2 weeks | Slight urine leakage during severe cough |
| 16 | Urine leakage during cough | 600 mg/day for 2 weeks | No urine leakage during severe cough |
| 17 | Urine leakage during jogging | 600 mg/day for 2 weeks | No urine leakage after 3 km of jogging |
| 18 | Urine leakage during jogging | 600 mg/day for 2 weeks | No urine leakage after 3 km of jogging |
| 19 | Urine leakage during jumping | 600 mg/day for 2 weeks | No urine leakage after 1500 times of rope skipping |

TABLE 2-continued

Experiment statistical table of pelvic floor
muscle rehabilitation people by postbiotic

| Serial number | Condition before taking | Dosage and use cycle | Condition after taking |
|---|---|---|---|
| 20 | Urine leakage during jumping | 600 mg/day for 2 weeks | No urine leakage after 1500 times of rope skipping |

Through the above effect verification experiments, it is showed that the postbiotic preparation prepared by the present disclosure has a strong pelvic floor muscle rehabilitation function.

Finally, it should be finally noted that the foregoing descriptions are merely exemplary embodiments of the present disclosure, but are not intended to limit the present disclosure. Although the present disclosure has been described in detail with reference to the foregoing embodiments, for a person of ordinary skill in the art, modifications can be made to the technical solutions described in the foregoing embodiments, or equivalent replacements can be made to some technical features in the technical solutions. Any modification, equivalent replacement, or improvement made and the like within the spirit and principle of the present disclosure shall fall within the protection scope of the present disclosure. The specific implementations of the present disclosure are described above, but are not intended to limit the protection scope of the present disclosure. A person skilled in the art should understand that various modifications or deformations may be made without creative efforts based on the technical solutions of the present disclosure, and such modifications or deformations shall fall within the protection scope of the present disclosure.

What is claimed is:

1. A microbial agent, comprising an inactivated strain of L. plantarum Nice-02, preserved in CCTCC (China Center for Type Culture Collection) on Apr. 21, 2023 with a biological preservation number of CCTCC NO: M 2023571; wherein the microbial agent is prepared by a method comprising:
   S1: activation culture: performing plate streaking on the L. plantarum Nice-02 into an activation culture medium to obtain a pure strain;
   S2: primary seed solution preparation: picking and placing a single colony of the L. plantarum Nice-02 prepared in S1 into a first culture solution at 28 to 30° C. for stationary culture for 12 to 14 h to obtain a primary seed solution;
   S3: secondary seed solution preparation: inoculating the primary seed solution into a second culture solution according to an inoculation amount of 0.1 to 5% for stationary culture at 30° C. to 40° C. for 10 to 12 h to obtain a secondary seed solution;
   S4: tertiary seed solution preparation: inoculating the cultured secondary seed solution into a seeding tank containing a third culture solution under an aseptic condition at an inoculation amount of 0.5 to 5%, and performing stir culture at a stirring speed of 20 to 50 r/min, a temperature of 30° C. to 40° C., a pH value of 7.0 and a tank pressure of 0.03 to 0.06 MPa to obtain a tertiary seed solution after the culture for 10 to 12 h;
   S5: L. Plantarum primary fermentation: inoculating the tertiary seed solution into a fermentation tank containing a sterilized culture solution at an inoculation amount of 0.5 to 5%, a temperature of 32° C., a stirring speed of 40 to 50 r/min to be cultured for 5 to 6 h;
   S6: L. plantarum secondary fermentation: after 5 to 6 h, lowering the fermentation temperature to 30° C., accelerating the stirring speed to 50 to 70 r/min, keeping the tank pressure at 0.05 MPa and the natural pH, and performing fermentation for 3 to 4 h;
   S7: L. plantarum tertiary fermentation: after 8 to 10 h, keeping the stirring speed unchanged, raising the fermentation temperature to 35° C., keeping the tank pressure at 0.05 MPa, keeping the pH value at 6.5, and performing fermentation for 2 h;
   S8: L. plantarum quaternary fermentation: after 10 to 12 h, decelerating the stirring speed to 30 to 40 r/min, raising the fermentation temperature to 40° C., keeping the tank pressure at 0.05 MPa and the pH value at 6.5, and performing fermentation for 1 to 2 h to obtain a fermentation solution; and
   S9: L. plantarum quinary fermentation: after 11 to 14 h, keeping the stirring speed unchanged, raising the temperature to 45° C., adding sterile lipoteichoic acid accounting for 0.05 to 0.2% of the volume of the fermentation solution into the fermentation tank, lowering the temperature to 20° C., and keeping the state for 30 min;
   wherein the microbial agent is obtained by performing high-temperature inactivation and spray drying the fermentation solution prepared in S9.

2. The microbial agent according to claim 1, wherein in S1,
   the activation culture medium is prepared from 0.05 to 0.2% of casein, 0.05 to 0.2% of sialic acid, 0.3 to 1.0% of beef extracts, 0.5 to 2% of peptone, 0.05 to 0.2% of sodium acetate, 0.05 to 0.2% of potassium dihydrogen phosphate and 1.5 to 2.0% of agar powder, and a pH value is adjusted to 7.0.

3. The microbial agent according to claim 2, wherein the activation culture medium is prepared from 0.1% of casein, 0.1% of sialic acid, 0.7% of beef extracts, 1% of peptone, 0.1% of sodium acetate, 0.1% of potassium dihydrogen phosphate and 2.0% of agar powder, and a pH value is adjusted to 7.0.

4. The microbial agent according to claim 1, wherein in S2,
   the first culture solution is prepared from 0.05 to 0.2% of casein, 0.05 to 0.2% of sialic acid, 1 to 5% of fructooligosaccharide, 0.1 to 1% of yeast powder, 0.05 to 0.2% of sodium acetate and 0.05 to 0.2% of potassium dihydrogen phosphate, and a pH value is adjusted to 7.0.

5. The microbial agent according to claim 4, wherein the first culture solution is prepared from 0.1% of casein, 0.1% of sialic acid, 3% of fructooligosaccharide, 0.5% of yeast powder, 0.1% of sodium acetate and 0.1% of potassium dihydrogen phosphate, and a pH value is adjusted to 7.0.

6. The microbial agent according to claim 1, wherein in S3, the second culture solution is prepared from 0.1 to 1% of casein, 0.05 to 0.2% of sialic acid, 1 to 3% of fructooligosaccharide, 0.1 to 1% of yeast powder and 0.05 to 0.2% of Tween-80, and a pH value is natural.

7. The microbial agent according to claim 6, wherein the second culture solution is prepared from 0.5% of casein, 0.1% of sialic acid, 1.5% of fructooligosaccharide, 0.5% of yeast powder and 0.1% of Tween-80, and a pH value is natural.

8. The microbial agent according to claim 1, wherein in S4, the third culture solution is prepared from 0.5 to 5% of peptone, 1 to 5% of isomaltooligosaccharide, 0.1 to 0.5% of dipotassium phosphate, 0.5 to 5% of glycine, 0.1 to 1% of tyrosine, 0.05 to 0.2% of Tween-80 and 0.05 to 0.2% of a polyether defoamer, and a pH value is natural.

9. The microbial agent according to claim 1, wherein the third culture solution is prepared from 1% of peptone, 4% of isomaltooligosaccharide, 0.2% of dipotassium phosphate, 1% of glycine, 0.5% of tyrosine, 0.1% of Tween-80 and 0.1% of a polyether defoamer, and a pH value is natural.

10. The microbial agent according to claim 1, wherein the culture solution used in a multi-stage fermentation process is prepared from 3% of isomaltooligosaccharide, 0.2% of casein, 2% of peptone, 5% of fructooligosaccharide, 3% of water-soluble starch, 0.1% of Tween-80, 0.5% of glycine, 0.5% of tyrosine and 0.2% of a polyether defoamer, and a pH value is natural.

11. A method for rehabilitating pelvic floor muscles, comprising administering an amount of a microbial agent according to claim 1 to a subject in need thereof, wherein the administration is performed orally or vaginally.

\* \* \* \* \*